United States Patent
Woolard et al.

(10) Patent No.: US 9,186,610 B2
(45) Date of Patent: Nov. 17, 2015

(54) ROOMSIDE REPLACEABLE FAN FILTER UNIT

(71) Applicant: CAMFIL USA, INC., Riverdale, NJ (US)

(72) Inventors: Keith G. Woolard, Washington, NC (US); Sean O'Reilly, West Palm Beach, FL (US)

(73) Assignee: CAMFIL USA, INC., Riverdale, NJ (US)

( * ) Notice: Subject to any disclaimer, the term of this patent is extended or adjusted under 35 U.S.C. 154(b) by 48 days.

(21) Appl. No.: 13/795,304

(22) Filed: Mar. 12, 2013

(65) Prior Publication Data

US 2014/0260981 A1    Sep. 18, 2014

(51) Int. Cl.
- *B01D 50/00* (2006.01)
- *B01D 46/00* (2006.01)
- *B01D 46/10* (2006.01)
- *B01D 46/52* (2006.01)

(52) U.S. Cl.
CPC ............ *B01D 46/0086* (2013.01); *B01D 46/10* (2013.01); *B01D 46/521* (2013.01); *B01D 2273/18* (2013.01)

(58) Field of Classification Search
None
See application file for complete search history.

(56) References Cited

U.S. PATENT DOCUMENTS

| | | | | |
|---|---|---|---|---|
| 4,193,778 A | * | 3/1980 | Strahsner et al. | 96/313 |
| 4,411,675 A | * | 10/1983 | de Castella | 96/140 |
| 5,620,503 A | * | 4/1997 | Miller et al. | 95/211 |
| 5,702,648 A | | 12/1997 | White et al. | |
| 6,267,793 B1 | | 7/2001 | Gomez et al. | |
| 6,312,504 B1 | * | 11/2001 | Both et al. | 95/214 |
| 6,367,278 B1 | | 4/2002 | Strussion et al. | |
| 6,368,393 B1 | * | 4/2002 | Hironaka | 96/111 |
| 6,387,165 B1 | * | 5/2002 | Wakamatsu | 96/270 |
| 6,517,612 B1 | | 2/2003 | Crouch et al. | |
| 7,210,363 B2 | * | 5/2007 | Morse et al. | 73/863.23 |
| 7,220,291 B2 | | 5/2007 | Morse et al. | |

(Continued)

OTHER PUBLICATIONS

Flanders Filters, Inc., Fan Filter Specification, Jan. 24, 2012.

(Continued)

*Primary Examiner* — Duane Smith
*Assistant Examiner* — Phillip Shao
(74) *Attorney, Agent, or Firm* — Patterson & Sheridan, LLP

(57) ABSTRACT

Embodiments described herein relate to roomside replaceable fan filter units. In one embodiment, a roomside replaceable fan filter unit includes a housing having a filter receiving aperture and an air inlet, an aerosol injector, and a fan filter unit. The fan filter unit is coupled to the housing between the aerosol injector and the filter receiving aperture. In another embodiment, a roomside replaceable fan filter unit includes a housing having a sidewalls and a top wall that define an interior volume, an air inlet formed in the top wall, and a filter receiving aperture disposed opposite the top wall. The roomside replaceable fan filter unit also includes a fan filter unit disposed in the interior volume between the air inlet and the filter receiving aperture. The roomside replaceable fan filter unit includes an aerosol injector disposed upstream of the fan filter unit in the interior volume.

18 Claims, 3 Drawing Sheets

(56) References Cited

U.S. PATENT DOCUMENTS

| | | | |
|---|---|---|---|
| 7,320,721 B2* | 1/2008 | Ham et al. | 55/498 |
| 7,971,857 B1 | 7/2011 | Mazza | |
| 2003/0205038 A1 | 11/2003 | Goyetche | |
| 2006/0112757 A1 | 6/2006 | Morse | |
| 2006/0272301 A1 | 12/2006 | Morse et al. | |
| 2006/0276120 A1 | 12/2006 | Cherry, Sr. et al. | |
| 2011/0011268 A1* | 1/2011 | Lee et al. | 96/371 |
| 2012/0246910 A1 | 10/2012 | Morse et al. | |

OTHER PUBLICATIONS

Flanders Filters, Inc., TH Series UL 900 Class 1, Factory Mutual Approved, Truly Separatorless Filter Modules, 2013, Bulletin: PB1500-0511.

American Air Filter Company, Inc., FM2-LE Self-Contained Energy Efficient Fan/Filter Modules for Cleanroom Applications, May 2010.

PCT international search report and written opinion of PCT/US14/10141 dated Apr. 16, 2014.

* cited by examiner

| 502 |
|---|
| REMOVING A USED FILTER FROM A FAN FILTER HOUSING |

| 504 |
|---|
| INSTALLING A REPLACEMENT FILTER IN THE FAN FILTER HOUSING |

| 506 |
|---|
| PULLING AIR INTO THE FAN FILTER HOUSING AND OUT THROUGH THE REPLACEMENT FILTER |

| 508 |
|---|
| PROVIDING AN AEROSOL AT A LOCATION ADJACENT AND UPSTREAM OF AN AIR MOVING BLADE OF A FAN |

| 510 |
|---|
| TESTING THE REPLACEMENT FILTER FOR LEAKS AND/OR FILTRATION EFFICIENCY |

FIG. 5

ROOMSIDE REPLACEABLE FAN FILTER UNIT

BACKGROUND OF THE INVENTION

1. Field of the Invention

Embodiments described herein relate to roomside replaceable fan filter units. More particularly, embodiments described herein relate to a roomside replaceable fan filter unit with an aerosol injection ring.

2. Description of the Related Art

Cleanrooms are utilized in many industries, for example pharmaceutical manufacturing facilities or biotechnology research labs, where clean space is a manufacturing or health-related requirement. A plurality of filters, typically mounted in the ceiling of the cleanroom as roomside replaceable filter units, are configured to remove particulate from air entering the cleanroom at a predetermined efficiency selected based upon the cleanliness requirements of the activities performed in the cleanroom.

The performance of the filters disposed in the roomside replaceable filter units is critical to for providing contaminant-free or hazardous-free air. Therefore, it is necessary to certify the performance (e.g., leak and/or filtration efficiency) of the filters by field testing on at least an annual basis to determine whether the filters are maintaining the proper filter efficiency. The certification process ensures that the filters are meeting predefined operations criteria and/or standards.

Typically a certification process includes challenging the filters with an upstream aerosol challenge to perform statistically valid tests. Most cleanrooms are configured to have a common plenum feeding multiple roomside filter units. In order to test one filter, enough aerosol must be provided to the entire plenum to have a sufficient uniform concentration for testing the filter. As such, large quantities of aerosol are needed to create a uniform concentration of aerosol within the plenum. The large quantity of aerosol needed to test a single filter is not only wasteful, but also undesirably loads the interested filters in communication with the plenum. Additionally, an undesirably high usage of aerosol, a long period of time is required to adequately charge and stabilize the aerosol concentration within the plenum, which undesirably reduces the availability of the clean room for normal operations.

Thus, there is a need for an improved roomside replaceable filter unit and method for testing filters used in the same.

SUMMARY OF THE INVENTION

Embodiments described herein relate to roomside replaceable fan filter units. In one embodiment, a roomside replaceable fan filter unit includes a housing, an aerosol injector, and a fan module. The housing has a filter receiving aperture adapted to receive a filter and an air inlet. The fan module is coupled to the housing and includes an air moving blade disposed between the aerosol injector and the filter receiving aperture.

In another embodiment, a roomside replaceable fan filter unit includes a housing having a plurality of sidewalls and a top wall that define an interior volume, an air inlet formed in the top wall, and a filter receiving aperture disposed opposite the top wall and adapted to receive a replaceable air filter. The roomside replaceable fan filter unit also includes a fan module disposed in the interior volume between the air inlet and the filter receiving aperture. The roomside replaceable fan filter unit further includes an aerosol injector coupled to the housing and disposed upstream of an air moving blade of the fan module.

In another embodiment, a method for utilizing a replaceable fan filter unit comprising an aerosol injector includes replacing a used filter from the fan filter unit with a replacement filter. The method also includes pulling air into a housing of the replaceable fan filter unit and pushing air out through the replacement filter by a fan module. The method further includes providing an aerosol challenge to the air through an aerosol injector coupled to the housing, wherein the aerosol injector is disposed upstream of an air moving blade of a fan module.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 4 is a top view of one embodiment of an aerosol injector; and

FIG. 5 is a flow diagram of one embodiment of a method for utilizing a roomside replaceable fan filter unit having an integral aerosol injection ring.

To facilitate understanding, identical reference numerals have been used, wherever possible, to designate identical elements that are common to the figures. It is contemplated that elements of one embodiment may be beneficially incorporated in other embodiments without further recitation.

DETAILED DESCRIPTION

Figure 1:
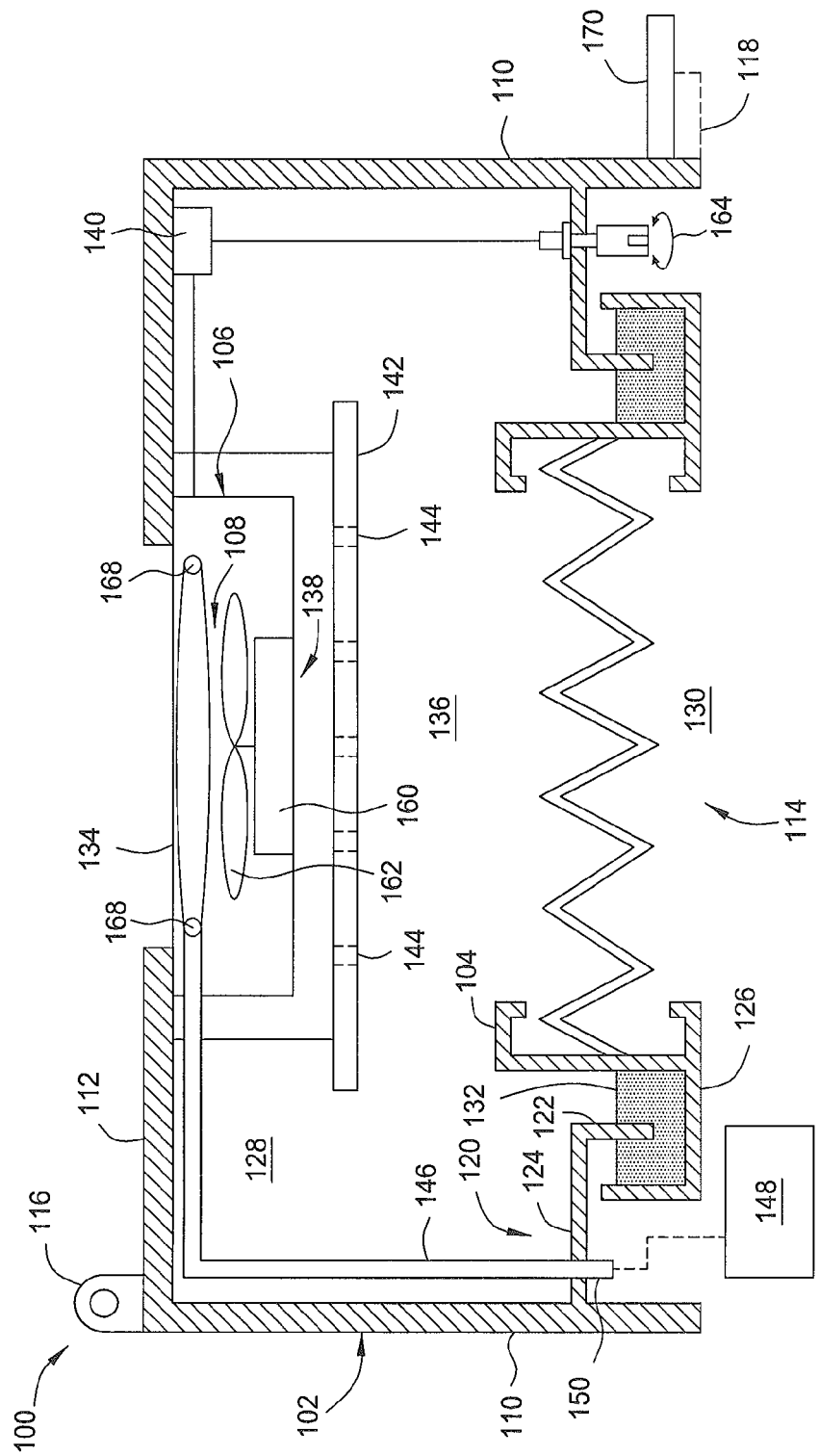
FIG. 1 is a sectional view of one embodiment of a roomside replaceable fan filter unit.

FIG. 1 depicts a sectional view of one embodiment of a roomside replaceable fan filter unit (fan filter unit 100) having a fan module 106 and an aerosol injector 108 integrated into a single unit that may be installed in a structure 170, such as a ceiling, wall or floor of a room, a machine enclosure, mini-environment or other surface bounding an area requiring delivery of filtered air. The integral aerosol injector 108 is located to provide aerosol into the airstream upstream of at least air moving blades of the fan module 106. The location of the integral aerosol injector 108 advantageously allows a single filter to be challenged for testing without having to provide aerosol to other filters as currently done in conventional applications. The fan filter unit 100 includes a filter housing 102 to which the fan module 106 and aerosol injector 108 are mounted. The filter housing 102 a plurality of sidewalls 110 and a top wall 112 that define an interior volume 136. The side of the sidewalls 110 opposite the top wall 112 terminate in a filter receiving aperture 114 configured to receive a replaceable filter 104. In one embodiment, the filter 104 may be a high-efficiency particulate air (HEPA) filter or an ultra-low penetration air filter, or any other suitable filter. The filter receiving aperture 114 is sized to allow the filter 104 to at least partially enter the housing 102, thereby allowing the filter 104 to be removed and replaced from the housing 102 as needed. The top wall 122 includes an inlet 134 which allows airs to enter the interior volume 136 of the filter housing 102 prior to flowing through the filter 104 and out of the filter housing 102 through the filter receiving aperture 114.

The sidewalls 110 and the top wall 112 of the filter housing 102 are generally fabricated from a rigid material, for example a metal material, such as aluminum or stainless steel. Other rigid materials suitable for fabricating the sidewalls 110 and the top wall 112 of the filter housing 102 include materials such as plastic, wood-based products, and glass reinforced plastic, among others. The sidewalls 110 are generally configured in a polygonal form, such as a square or rectangle. The sidewalls 110 are sealingly coupled together at their intersections, for example, by welding, riveting, soldering, adhering, bonding, caulking and the like. The top wall 112 is generally coupled to the sidewalls 110 in a similar fashion to make the filter housing 102 leak-tight.

In one embodiment, the sidewalls 110 and/or the top wall 112 includes a mounting pad or tab 116 that facilitates coupling the filter housing 102 to a supporting structure (not shown) for disposing the fan filter unit 100 above a room, such as a cleanroom. In some locations, the tab 116 is required as a seismic restraint.

In another embodiment, a flange 118 (shown in phantom) may extend outwards from the sidewalls 110 to interface with the structure 170. The flange 118 may be coupled and/or sealed to the structure 170. The flange 118 may be caulked or sealed with a gasket to the structure 170.

A sealing element 120 extends from the sidewalls 110 into the interior volume 136 adjacent the filter receiving aperture 114. The sealing element 120 provides a substantially air-tight seal between the filter 104 and the housing 102. In one embodiment, the sealing element 120 includes a knife edge 122 that is coupled to sidewall 110 by a sealing flange 124. The knife edge 122 and the sealing flange 124 may be fabricated from a single piece of material to prevent air by-pass, and may also be fabricated with the sidewall 110 as a continuous piece of material as shown in FIG. 1, for example, as an extrusion. The knife edge 122 is orientated substantially parallel to the sidewalls 110 and is configured to interface with a sealing face 126 disposed at one end the filter 104 to create an air-tight seal between the filter housing 102 and the filter 104 upon installation of the filter 104 into the filter housing 102. Thus, the sealing element 120 separates the interior volume 136 of the filter housing assembly 102 into a plenum 128 defined between the sealing element 120 and the top wall 112 that is upstream of the filter 104 and a filter receiving portion 130 in which the filter 104 mounts. In other words, the filter 104 interfacing with the sealing element 120 separates the unfiltered air disposed in the plenum 128 defined upstream of the filter 104 with the clean, filtered air, downstream of the filter 104.

In the embodiment depicted in FIG. 1, the sealing face 126 includes a trough 132 circumscribing the perimeter of the filter 104. The trough 132 is at least partially filled with a gel, such as silicone or polyurethane gel. As the filter 104 is move into the filter receiving portion 130, the knife edge 122 of the housing 102 penetrates the gel to create an air seal between the filter 104 and the filter housing 102. The filter 104 is secured in the filter housing 102 in a position that ensures engagement between the sealing face 126 and sealing element 120 by a filter retainer, such as a pawl tab (not shown) mounted to the sealing flange 124. The filter retainer may alternatively be a screw, nut, clip, quarter turn fastener or other element suitable for releasably retaining the filter 104 in the housing 102.

Figure 2:
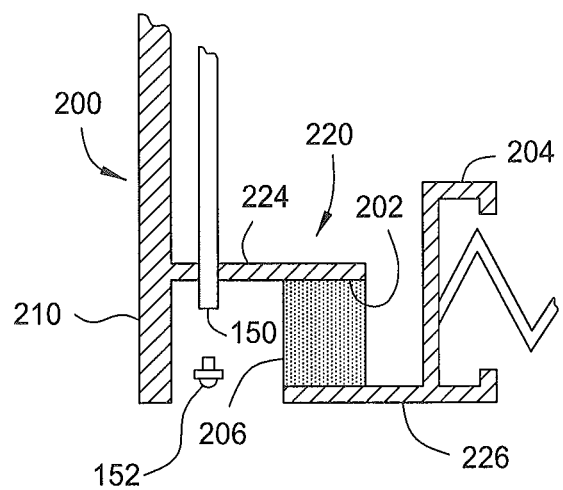
FIG. 2 is a partial sectional view of an alternative embodiment of a sealing section of a filter housing.

FIG. 2 depicts a partial sectional view a housing 200 illustrating an alternative sealing element 220 which may be utilized to form the fan filter unit 100. Sidewalls 210 of the housing 200 are generally similar to the sidewalls 110 described above with reference to FIG. 1. The sealing element 220 includes a sealing flange 224 that extends perpendicularly inward from the sidewall 210 to provide a planar gasket seating surface 202. A filter 204 having a gasket 206 disposed on top of a portion of a sealing face 226 is urged against the sealing flange 224, thereby compressing the gasket 206 against the sealing flange 224 to provide a seal between the housing 200 and filter 204. It is contemplated that the gasket 206 may be alternatively coupled to the sealing flange 204 of the housing 200.

Referring back to FIG. 1, the fan module 106 is coupled to the filter housing 102. In one embodiment, the fan module 106 is mounted at least partially or completely inside the interior volume 136 of the filter housing 102. The fan module 106 is configured to draw air through the inlet 134 of the filter housing 102 and into the plenum 128, the air ultimately flowing through the filter 104 and into the room downstream of the filter 104. The fan module 106 includes a fan 138 and a controller 140. The fan 138 includes a motor 160 and blades 162 for moving the air. The controller 140 is configured to control the operational speed of the fan 138 so that the amount of air flowing through the filter housing 102 and out the filter 104 may be set as desired. In the embodiment seen in FIG. 1, the controller 140 is located internally on the filter housing 102. However, it is contemplated that the controller 140 may be located in any suitable location, either coupled to, or remotely from, the housing 102.

The controller 140 may includes a fan speed adjustment control 164 exposed to the roomside of the filter housing 102 so that the speed of the fan 138 may be easily set. For example, the fan speed adjustment control 164, such as a control knob, may sealingly penetrate through the sealing flange 124 in a location accessible between the installed filter 104 and the sidewalls 110 of the filter housing 102. It is contemplated that the adjustment control 164 may be located in other locations, either attached or remote from the housing 102, and that in some embodiments, the speed of the fan 138 may be set electronically without the use of a manual adjustment (e.g., adjustment control knob 164), for example, by using a remotely located computing device or other remote controller.

Figure 3:
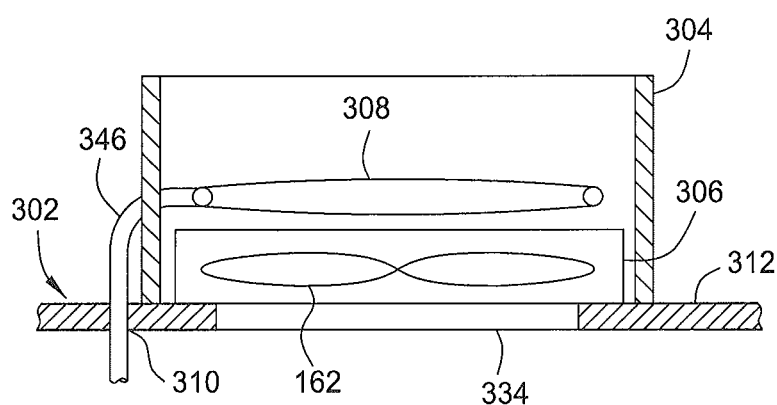
FIG. 3 is a partial sectional view of an alternative location for a fan module of a roomside replaceable fan filter unit.

In another embodiment, a fan module 306 may be mounted externally on the filter housing 302 as illustrated in FIG. 3. The fan module 306 is generally similar to the fan module 106 described above with reference to FIG. 1. In one embodiment, at least one of the housing 302 or the fan module 306 includes an optional collar 304 that is configured to mate with ductwork (not shown) that provides air to an inlet 334 formed through a top wall 312 of the filter housing 302.

Referring back to FIG. 1, the filter housing 102 may optionally include a diffuser plate 142 disposed in the interior volume 136. The diffuser plate 142 is generally a baffle utilized to redirect airflow within the plenum 128. In one embodiment, the diffuser plate 142 is positioned in the plenum 128 below the fan module 106 and is configured to enhance the uniform distribution of air within the plenum 128 to enhance flow uniformity exiting the filter 104.

The diffuser plate 142 may be fabricated from a metal or plastic material. The diffuser plate 142 may be a solid sheet or may be perforated. The diffuser plate 142 may also be planar, conical, curved or have another form. In the embodiment depicted in FIG. 1, the diffuser plate 142 includes optional apertures 144 to allow at least some air to flow therethrough.

The aerosol injector 108 is utilized to introduce an aerosol challenge within the filter housing 102 upstream of the filter 104. The aerosol injector 108 is positioned upstream of the air moving blades 162 of the fan module 106, for example, on a side of the fan module 106 opposite the sealing element 120. The aerosol injector 108 may be positioned inside or upstream of the fan module 106. By positioning the aerosol injector 108 upstream of the air moving blades 162 of the fan module 106, the blades 162 of the fan module 106 contribute to uniformly mixing the aerosol in the air entering the plenum 128, thereby allowing a smaller plenum 128 and in some cases, eliminating the need for diffuser plate 142, which allows smaller housing side walls 210, thereby reducing the size and cost of the filter housing 102. Additionally, as each fan filter unit 100 has its own aerosol injector 108, a single filter may be challenged for testing without having to provide aerosol to other filters as currently done in plenum ceiling applications, thereby providing a significant reduction in the amount of aerosol utilized and without unnecessarily loading filters not currently undergoing test with aerosol which reduces filter life.

The aerosol injector 108 includes one or more ports or nozzles (shown as 402 in FIG. 4) which are positioned to dispense aerosol into the airstream entering the housing 102 through the fan module 106. In one embodiment, the aerosol injector 108 includes a tube 168 positioned inside the filter housing 102 between the inlet 134 and the fan module 106. In one embodiment depicted in FIGS. 1 and 4, the aerosol injector 108 is tube 168 formed in a ring and having a plurality of ports 402. In one embodiment, the ports 402 are distributed around the tube 168, for example in a polar array. This beneficially provides a uniform distribution of the aerosol through the ports 402 and into the filter housing 102. The ports 402 formed in the aerosol injector 108 have an orientation which directs a spray 404 of aerosol into the filter housing 102 such that the spray is directed into the airstream rather than against a solid surface. In one embodiment, the ports 402 are oriented at an inward angle (e.g., towards the centerline of the inlet 134 of the filter housing 102), as shown in FIG. 4. However, in other embodiments, the ports 402 may be oriented at an upward, downward or outward angle. The fan module 106 moves the aerosol laden air into the plenum 128. As discussed above, the action of the blades 162 of the fan module 106, along with the optional diffuser plate 142 and/or other baffles provide adequate aerosol mixing of the aerosol laden air so that filter leak-testing may be performed. In one example, the fan module 106 provides sufficient mixing to allow ANSI or IEST leak-testing protocols to be performed, which will be discussed below further in detail.

An aerosol delivery tube 146 is routed through the plenum 128 of the filter housing 102. The aerosol delivery tube 146 is coupled to the aerosol injector 108. The aerosol delivery tube 146 terminates at an aerosol access port 150 accessible from the roomside, e.g., filter receiving aperture side, of the housing 102. In one embodiment, the aerosol access port 150 extends through the sealing flange 124 of the housing 102. The aerosol access port 150 is utilized to connect the aerosol injector 108 to an aerosol generator 148. It is contemplated, however, that the aerosol access port 150 may be positioned on other parts of the filter housing 102. The aerosol access port 150 is generally sealable, either through an internal check valve or with a stopper 252, as illustrated removed from the port 150 in FIG. 2. The aerosol generator 148 is utilized to supply an aerosol challenge to the upstream side of the filter 104 in the plenum 128 to enable a statistically valid test of the filter 104.

Injecting aerosol directly at the inlet 134 into the fan filter unit 100 advantageously reduces the amount of aerosol required for field testing, increases the uniformity of aerosol distribution adjacent the filter, and also allows field certifying technicians to accurately meet leak-testing protocols from roomside of the housing 102. Since the aerosol is provided to the aerosol access port 150 of a specific fan filter unit 100, each fan filter unit 100 can be tested individually from the roomside of the housing 102 without interrupting the normal operation of adjacent fan filter units 100. In one embodiment, the aerosol is injected between the between the inlet 134 and the fan module 106 on upstream of the filter 104. Since the aerosol is injected in a distributed manner across the air stream prior to encountering the spinning fan blades 162, the blades 162 more thoroughly mix the aerosol so that the air distributed inside the plenum 128 of the housing 102 has a much more uniform distribution of aerosol concentration than if only one point of aerosol injection (e.g., a single nozzle) was utilized.

The above described aerosol injection process ensures that the filter 104 is uniformly challenged across its plan area with substantially the same aerosol concentration. This uniform mixture beneficially ensures that the filter 104 can be accurately scan tested. To ensure the filter 104 is being challenged with a uniform aerosol laden air mixture, it is important to conduct factory qualification testing in accordance with industry accepted standards and test methods. An exemplary standard is IEST-RP-CC0034.2, HEPA and ULPA Filter Leak Tests, which requires that the airstream on the upstream side of the tested filter 104 be sampled in multiple locations and analyzed for uniformity. The standard sets parameters for the testing and pass/fail criteria. In one embodiment, during qualification testing of the fan filter unit 100, various methods of injecting aerosol were trialed, but the methods described herein gave a consistent uniform air-aerosol challenging mixture.

Comparative Results

A first method of injecting aerosol used a simple single point injecting location at a center of an inlet of the fan module within a mult-port aerosol injector. This method gave inconsistent results, because the injected aerosol stream followed inlet air streamlines to one side of the centerline of the fan module, and thus the aerosol was unevenly distributed inside the fan filter unit plenum. The highest challenge concentration of the aerosol corresponded to a side of the fan module in which the aerosol streamlined. Moving the injection point of the aerosol eccentrically off center of the inlet of the fan module did not improve the results. Although the injection point was directly over the center of the inlet of the fan module, the aerosol still streamlined inconsistently to various sides of the inlet of the fan module.

The next method to trial was to use the multi-port aerosol injector 108 to evenly distribute the aerosol into the inlet of the fan module 106 by injecting aerosol in multiple locations around the perimeter of the fan module 106, as discussed above. This method allowed the aerosol to follow the streamlines of the inlet of the fan module 106, however, allowed multiple streamlines to be challenged with the same volume of aerosol. This resulted in a much more uniform aerosol laden air mixture upstream of the filter 104. The test results for this injection method showed beneficial results.

For example, using IEST-RP-CC034.2 testing standards, a 100 mm pleat height MEGALAM® panel filter was tested at: (i) 485 cubic feet/min, (ii) 540 cubic feet/min, and (iii) 600 cubic feet/min with an upstream aerosol concentration of approximately 50 micrograms/liter using 10 sampling points that were located at various locations across the upstream face of the filter 104. The results respectively indicated: (i) an average concentration of 53 micrograms/liter at the sampling points with a standard deviation of 3 and a relative standard deviation of 0.05, (ii) an average concentration of 49 micrograms/liter at the sampling points with a standard deviation of 3 and a relative standard deviation of 0.07, and (iii) an average concentration of 56 micrograms/liter at the sampling points with a standard deviation of 4 and a relative standard deviation of 0.07, wherein the relative standard deviation acceptance criteria is less than 0.20.

In another example using IEST-RP-CC034.2 testing standards, a 50 mm pleat height MEGALAM® panel filter was tested at: (i) 485 cubic feet/min, (ii) 540 cubic feet/min, and (iii) 600 cubic feet/min with an upstream aerosol concentration of approximately 50 micrograms/liter using 10 sampling points that were located at various locations across the upstream face of the filter 104. The results respectively indicated: (i) an average concentration of 51 micrograms/liter at the sampling points with a standard deviation of 1 and a relative standard deviation of 0.03, (ii) an average concentration of 52 micrograms/liter at the sampling points with a standard deviation of 2 and a relative standard deviation of 0.04, and (iii) an average concentration of 52 micrograms/liter at the sampling points with a standard deviation of 2 and a relative standard deviation of 0.04, wherein the relative standard deviation acceptance criteria is less than 0.20.

Referring back to FIG. 3, an aerosol injector 308 may be positioned above the fan module 306, for example, in the collar 304. The aerosol injector 308 is coupled by a tube 346 to the aerosol access port 150 (not shown in FIG. 3). The aerosol injector 308 and tube 346 are generally similar to the aerosol injector 108 and tube 346 described above with reference to FIG. 1. The tube 346 may be routed either completely within the housing 302 or at least partially outside the housing 302. In the embodiment depicted in FIG. 3, the tube 346 is coupled to the aerosol injection ring 308, then runs external to the filter housing 302 prior to entering the housing 302 through an opening 310. The tube 346 may be sealed by a o-ring, gasket or caulk to the housing 302 to form an airtight seal at the opening 310.

FIG. 5 is a flow diagram of one embodiment of a method 500 for utilizing a roomside replaceable fan filter unit having an integral aerosol injector ring. At step 502, a used filter is removed from the fan filter unit housing installed in a structure, such as a ceiling of a clean room, mini-environment, machine enclosure or other boundary of a clean space. At step 504, a replacement air filter is installed in housing. At step 506, a fan pulls air into housing and out through the replacement filter. At step 508, an aerosol challenge is provided to the air flowing in the housing by the integral aerosol injector ring at a location adjacent and upstream of an air moving blade of the fan. At step 510, the replacement filter is tested for leaks and/or filtration efficiency by measuring the aerosol content at a location downstream of the replacement filter.

While the foregoing is directed to embodiments of the invention, other and further embodiments of the invention may be devised without departing from the basic scope thereof, and the scope thereof is determined by the claims that follow.

The invention claimed is:

1. A roomside replaceable fan filter unit comprising:

a housing having an air inlet and a filter receiving aperture, wherein the filter receiving aperture is adapted to sealingly engage a filter and is oriented to expose the filter disposed in the filter receiving aperture to a roomside of a structure to which the housing is mounted;

an aerosol injector; and a fan filter unit coupled to the housing, an air moving blade of the fan filter unit disposed between the aerosol injector and the filter receiving aperture.

2. The roomside replaceable fan filter unit of claim 1, wherein the housing comprises:

a plurality of sidewalls and a top wall that define an interior volume.

3. The roomside replaceable fan filter unit of claim 2, wherein the fan filter unit is disposed at least partially in the interior volume.

4. The roomside replaceable fan filter unit of claim 2, wherein the fan filter unit is disposed at least partially outside of the interior volume.

5. The roomside replaceable fan filter unit of claim 1, wherein a collar configured to mate with ductwork is coupled to one of the housing and fan filter unit.

6. The roomside replaceable fan filter unit of claim 5, wherein the aerosol injector is disposed in the collar.

7. The roomside replaceable fan filter unit of claim 1, wherein the aerosol injector is a tube.

8. The roomside replaceable fan filter unit of claim 1, wherein the aerosol injector is a ring.

9. The roomside replaceable fan filter unit of claim 1, wherein the aerosol injector comprises a plurality of holes.

10. The roomside replaceable fan filter unit of claim 9, wherein the plurality of holes face radially inward towards a centerline of the air inlet.

11. The roomside replaceable fan filter unit of claim 1, wherein the housing comprises an aerosol injection port coupled to the aerosol injector, and wherein the aerosol injection port is accessible from a side of the housing having the filter receiving aperture.

12. The roomside replaceable fan filter unit of claim 11, wherein the aerosol injection port is disposed through a sealing element of the housing-configured to sealingly engage the filter disposed in the filter receiving aperture.

13. The roomside replaceable fan filter unit of claim 1, wherein a filter is disposed in the filter receiving aperture.

14. A roomside replaceable fan filter unit comprising:

a housing comprising:

a plurality of sidewalls and a top wall that define an interior volume;

an air inlet formed in the top wall;

a filter receiving aperture disposed opposite the top wall and adapted to sealingly engage a filter and is oriented to expose the filter to a roomside of a structure to which the housing is mounted;

a fan filter unit disposed between the air inlet and the filter receiving aperture; and an aerosol injector disposed upstream of an air moving blade of the fan filter unit.

15. The roomside replaceable fan filter unit of claim 14, further comprising:

an aerosol delivery tube coupled to the aerosol injector, wherein the aerosol delivery tube comprises an aerosol access port accessible from outside of the housing.

16. The roomside replaceable fan filter unit of claim 14, wherein the aerosol injector is disposed in the fan filter unit.

17. The roomside replaceable fan filter unit of claim 1, wherein a diffuser plate is disposed between the fan filter unit and the filter receiving aperture.

18. The roomside replaceable fan filter unit of claim 1, wherein the filter is replaceable from the roomside of the filter receiving aperture.

* * * * *